(12) United States Patent
Gustin

(10) Patent No.: US 7,798,855 B2
(45) Date of Patent: Sep. 21, 2010

(54) CONNECTOR FOR SENSOR ASSEMBLY

(75) Inventor: Ronald R. Gustin, Washington, IL (US)

(73) Assignee: Caterpillar Inc, Peoria, IL (US)

( * ) Notice: Subject to any disclaimer, the term of this patent is extended or adjusted under 35 U.S.C. 154(b) by 176 days.

(21) Appl. No.: 11/956,847

(22) Filed: Dec. 14, 2007

(65) Prior Publication Data
US 2009/0156045 A1 Jun. 18, 2009

(51) Int. Cl.
*H01R 12/00* (2006.01)

(52) U.S. Cl. ............... 439/620.01; 439/620.21; 439/913

(58) Field of Classification Search ............ 439/620.01, 439/620.21, 913
See application file for complete search history.

(56) References Cited

U.S. PATENT DOCUMENTS

| | | | |
|---|---|---|---|
| 3,091,750 A | 5/1963 | Long et al. | |
| 4,308,518 A | 12/1981 | Hattori et al. | |
| 4,983,271 A | 1/1991 | Kato et al. | |
| 5,246,562 A | 9/1993 | Weyl et al. | |
| 5,573,650 A | 11/1996 | Fukaya et al. | |
| 6,238,226 B1 | 5/2001 | Schempp et al. | |
| 6,311,543 B1 | 11/2001 | Yoshikawa et al. | |
| 6,322,681 B1 | 11/2001 | Weyl | |
| 6,346,179 B1 | 2/2002 | Makino et al. | |
| 6,383,353 B1 | 5/2002 | Akatsuka et al. | |
| 6,401,521 B1 | 6/2002 | Nelson | |
| 6,484,561 B2 | 11/2002 | Jackson et al. | |
| 6,527,573 B2 | 3/2003 | Stein, Sr. et al. | |
| 6,658,918 B2 | 12/2003 | Hibino et al. | |
| 6,878,252 B2 | 4/2005 | Weyl et al. | |
| 7,032,433 B2 | 4/2006 | Hayashi et al. | |
| 7,191,640 B2 | 12/2007 | Weyl et al. | |
| 7,425,138 B2 * | 9/2008 | Buhl et al. | ............ 439/76.1 |
| 2006/0288759 A1 | 12/2006 | Okumura et al. | |
| 2007/0119235 A1 | 5/2007 | Matsuo et al. | |

FOREIGN PATENT DOCUMENTS

| | | |
|---|---|---|
| EP | 0836094 | 4/1998 |
| EP | 1394536 | 3/2004 |

* cited by examiner

*Primary Examiner*—Gary F. Paumen
(74) *Attorney, Agent, or Firm*—Leydig, Voit & Mayer

(57) ABSTRACT

A connector for a sensor assembly having sensing element with a non-conductive body including a plurality of spaced conductive contact pads arranged on opposite faces. A plurality of terminal contacts, each of which is in contact with one of the contact pads are supported in overlying relation to the contact pads on carriers. A separable biasing containment bracket is disposed in surrounding relation to the carriers and includes spring elements urging the carriers and terminal contacts toward the contact pads. A retaining band is interposed between the carriers and the spring elements.

20 Claims, 4 Drawing Sheets

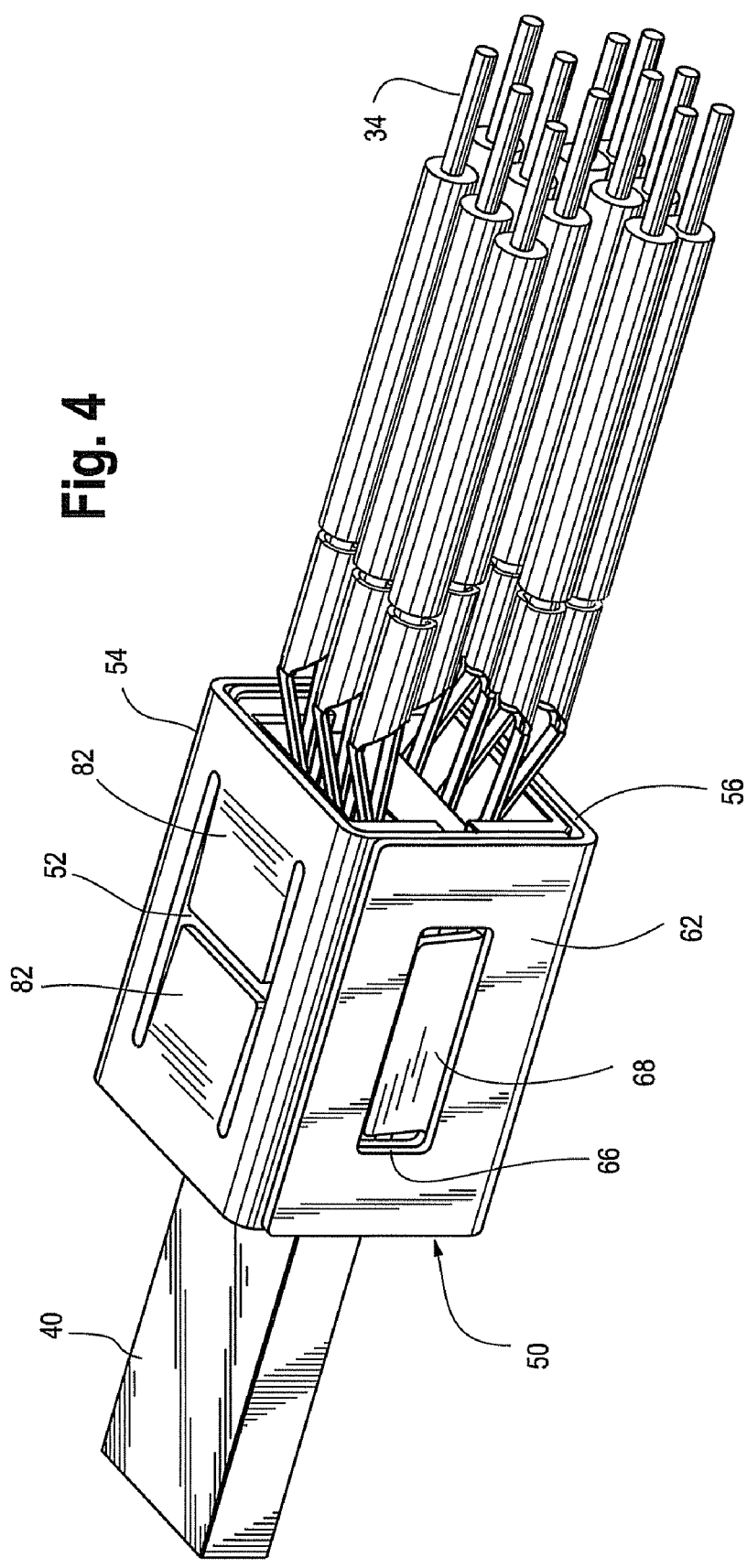
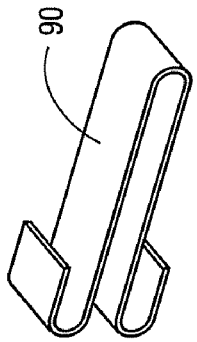

CONNECTOR FOR SENSOR ASSEMBLY

TECHNICAL FIELD

This patent disclosure relates generally to connectors for sensors used in measuring the chemical makeup and/or physical character of a test medium and, more particularly, to connectors for maintaining the integrity of the contact between the sensing element and electrical conductors for transmission of signals from the sensing zone.

BACKGROUND

It is generally known to use sensors such as oxygen sensors, pH meters, thermocouples and the like to measure one or more chemical properties and/or physical characteristics of a test medium. Such sensors are typically constructed to produce varying electromotive forces, electrical resistance values or another measurable electrical characteristic in response to the constituent or property being measured. By way of example only, an oxygen sensor may utilize a sensing element incorporating a galvanic cell in which a measurement electrode is exposed to a test medium while a reference electrode is isolated from the medium. The difference in electromotive force between the electrodes is then correlated to the oxygen potential in the test medium. In a thermocouple, a sensing element may incorporate two wires having different alloy compositions. These wires exhibit different electrical voltage characteristics when exposed to a common temperature gradient. Thus, measuring the relative difference in voltage between the wires is used to determine temperature.

In sensing systems that utilize the transmission of electrical data, signals may be transmitted between the sensing element and one or more units providing other functions such as monitoring units, control units or the like. This transmission may be carried out across a separable electrical connector including contact pads on the sensing element and terminal contacts associated with the conductors of the sensing circuitry. High vibration and high temperature environments may have adverse effects on the integrity of the electrical connection. It is useful to utilize an electrical connector assembly that mitigates the effects of vibration, temperature or other forces.

U.S. Pat. No. 4,983,271 to Kato et al. issued Jan. 8, 1991, discloses an oxygen sensor incorporating a multi-lead electrical connection between a sensor element and lead wires. The electrical connector disclosed in U.S. Pat. No. 4,983,271 includes a plurality of sensing electrodes carried on an end of a plate type ceramic sensor element. The electrodes are in electrical communication, within the sensor element, with an equal number of conductive contact pads exposed at the planar faces at the opposite end of the sensing element.

Conductor terminal contacts attached to wire conductors are supported on a pair of ceramic carriers overlying the conductive contact pads. A surrounding metallic fitting includes outwardly extending leaf springs. The spring leafs are compressed by a surrounding caulking ring crimped about the assemblage to deform the springs. The carriers are urged toward the sensor element to urge the terminal contacts into contact with the contact pads.

In the system of Kato et al., the leaf springs bias against an inwardly deformed caulking ring surrounding the fitting and carriers such that the fitting is maintained in compressed relation against the ceramic carriers. The deformed caulking ring presses the leaf springs inwardly toward the fitting which exerts a compressive force against the carriers.

While a system such as disclosed in Kato et al. may be fully functional, the use of a caulking ring may give rise to some limitations. By way of example, in the event that components are misaligned or if the caulking ring is incorrectly located, the sensor element may be difficult to salvage once the caulking ring is crimped. Likewise, the difficulty of removing the pressed caulking ring may make parts difficult to recondition. Moreover, there is an inherent variability involved in compressing the caulking ring in place against the leaf springs.

Accordingly, an improved electrical connector, which reduces variability and which facilitates reconditioning for use in a sensor assembly is desirable.

SUMMARY

In accordance with one aspect, the present disclosure provides an electrical connector for sensor assembly comprising a sensing element having a non-conductive body including a plurality of spaced conductive contact pads arranged thereon; a plurality of conductive terminal contacts, each one being in contact with one of the spaced contact pads; at least one carrier supporting the terminal contacts in contacting relation to the contact pads; a containment bracket surrounding the at least one carrier and the contact pads; the bracket including at least one biasing element extending from the bracket toward the at least one carrier urging the at least one carrier toward the contact pads.

In another aspect, the present disclosure provides sensor assembly comprising: a sensor housing; a connector within the sensor housing comprising a sensing element having a non-conductive body including a plurality of spaced conductive contact pads arranged thereon; a plurality of conductive terminal contacts, each one being in contact with one of the spaced contact pads; at least one carrier supporting the terminal contacts in contacting relation to the contact pads; a containment bracket surrounding the at least one carrier and the contact pads; the bracket including at least one biasing element extending from the bracket toward the at least one carrier urging the at least one carrier toward the contact pads.

In accordance with another aspect, the present disclosure provides a method of assembly for a sensor assembly having a connector for a sensor assembly, the steps comprising providing a sensing element having a non-conductive body including a plurality of spaced conductive contact pads arranged thereon; providing a plurality of conductive terminal contacts, for contact with one of the spaced contact pads; providing at least one carrier for supporting the terminal contacts in contacting relation to the contact pads; providing a containment bracket for surrounding the at least one carrier and the contact pads; the bracket including at least one biasing element extending from the bracket and toward the at least one carrier for urging the at least one carrier toward the contact pads; attaching the terminal contacts to the at least one carrier; positioning the at least one carrier with the terminal contacts in contact with the plurality of spaced contact pads; surrounding the spaced contact pads and the at least one carrier with the containment bracket; and causing the at least one biasing element to urge the at least one carrier toward the spaced contact pads of the sensing element.

BRIEF DESCRIPTION OF THE DRAWINGS

FIG. 4 is a schematic view illustrating the containment bracket in assembled condition in surrounding relation to a multi-lead electrical connector of the sensor of FIG. 1;

FIG. 5 is a schematic view of a removable pre-assembly plug used in connection with the electrical connector of the sensor of FIGS. 1-4.

DETAILED DESCRIPTION

This disclosure relates to an improved connector for a sensor assembly incorporating a plate shaped sensing element with a plurality of spaced conductive contact elements or pads. A plurality of electrical conductors include terminal contacts supported upon insulated carriers. The terminal contacts are urged into contact with the conductive contact pads on the sensing element by a biasing containment bracket.

Figure 1:
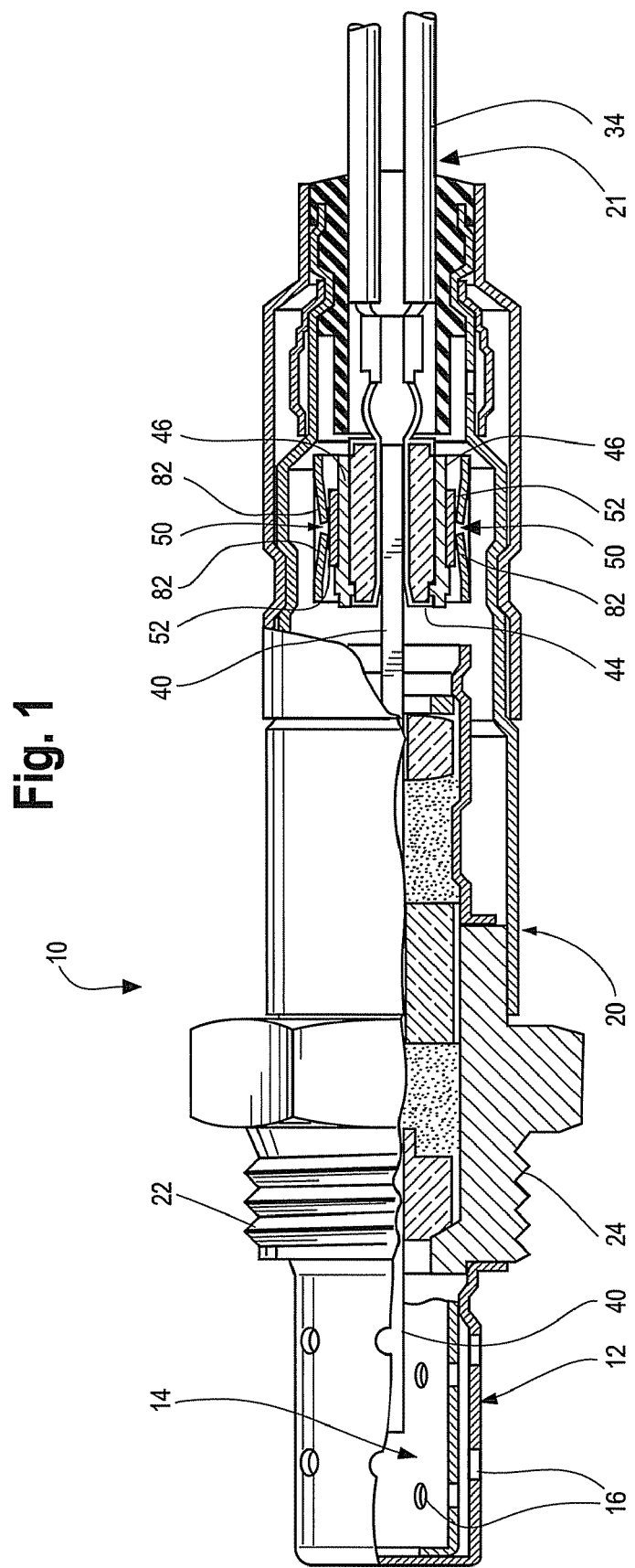
FIG. 1 is a cut-away plan view illustrating an oxygen sensor incorporating a multi-lead electrical connector.

Reference will now be made to the drawings wherein, to the extent possible, like elements are designated by like reference numerals throughout the various views. FIG. 1 illustrates an exemplary sensor assembly 10 such as an oxygen sensor or the like. It is to be understood that the sensor 10 shown in FIG. 1 is presented for exemplary and explanatory purposes only and that the present disclosure is in no way limited to any particular type of sensor. Rather, it is contemplated that concepts and features consistent with this disclosure may have broad applicability to any number of sensor devices.

As shown, the sensor assembly 10 includes a sensor housing 20 including probe section 12 adapted for placement within a medium to be analyzed, such as a gaseous or liquid fluid stream or the like. In the illustrated construction, the probe section 12 defines a chamber 14 with transport openings 16 to engage the environment surrounding probe section 12.

The housing 20 may be formed from metal or other suitable material as may be desired. As shown, the housing includes a threaded lower neck portion 22 to permit sensor 10 to be secured to the wall of a chamber such as an exhaust manifold (not shown). The sensor includes an opposite end 21 arranged to provide an exit for electrical conductors 34 connected to the circuitry (not shown) involved in the monitoring function.

Figure 2:
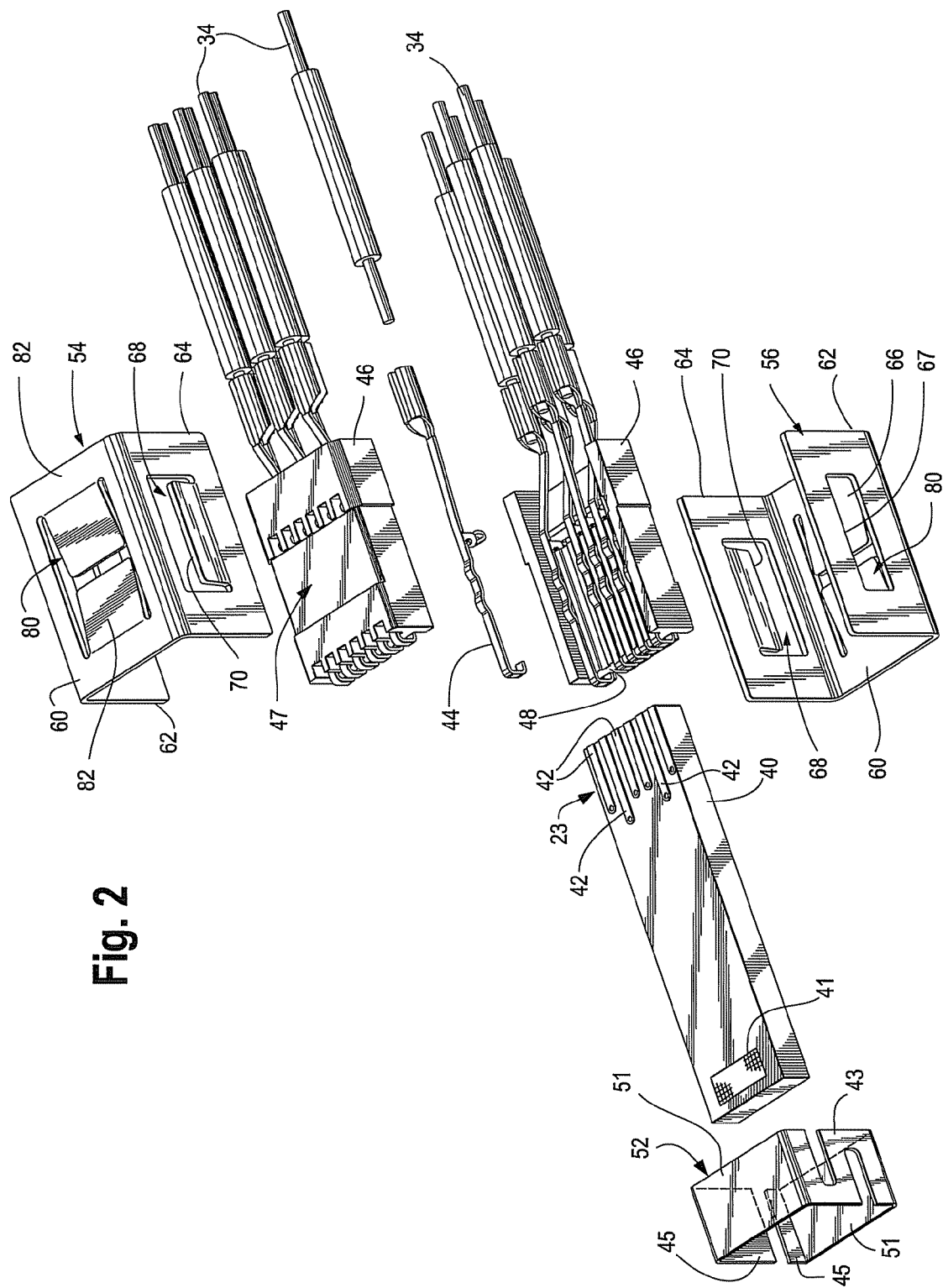
FIG. 2 is an exploded, schematic view illustrating components of an exemplary multi-lead electrical connector of the sensor of FIG. 1.
Figure 3:
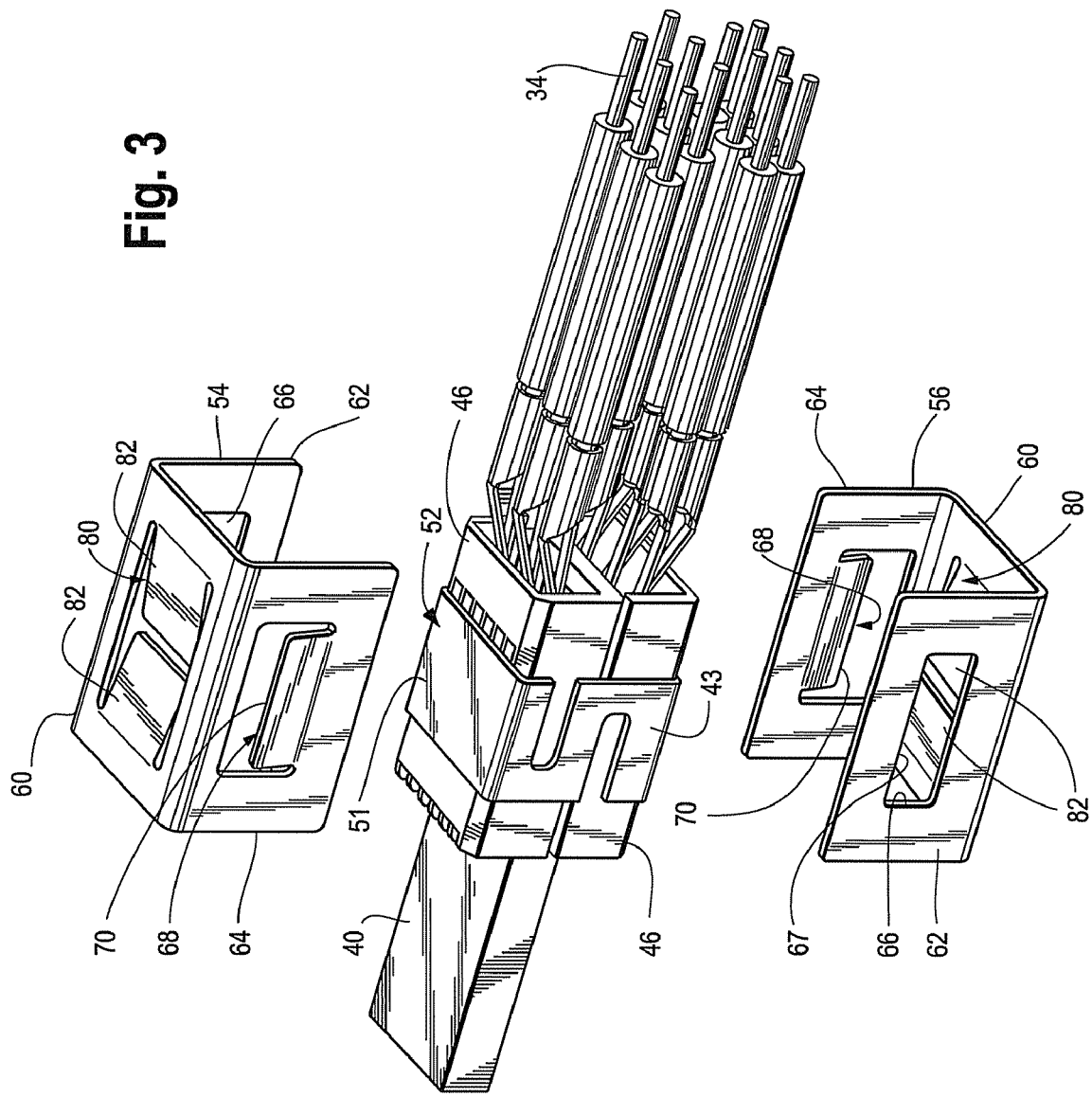
FIG. 3 is a schematic view illustrating an exemplary placement of a retaining band and separable containment bracket relative to a multi-lead electrical connector of the sensor of FIG. 1.

As best illustrated in FIGS. 2-4, an elongate plate shaped sensing element 40 is contained within body 20. It extends from a first end having at least one sensing surface or screen 41 exposed to the medium in chamber 14, to a second distal end near conductor exit end 21. Appropriate non-conductive material such as crushed ceramic, supports the sensing element 40 in body 20 and isolates the chamber 14 from the remainder of the interior of the sensor body.

The sensing element 40 may be formed from a suitable nonconductive material such as plastic, or ceramic, or such other material as may be desired. A plurality of contact pads 42, seen in FIG. 2, are arranged in spaced relation across opposing planar surfaces at the distal end 23 of sensing element 40. In this regard, it is to be understood that the pattern of spaced contact pads extending across the upper planar surface of sensing element 40, viewable in FIG. 2, and another pattern of spaced contact pads is likewise disposed across the opposing lower planar surface.

A pair of carriers 46 overlie the planar surfaces of the sensing element at distal end 23 containing the spaced conductive contact pads 42. The carriers are non-conductive and made from ceramic or other suitable material. Carriers 46 each include an outer planar surface 47 and an inner surface 48 facing the contact pads 42. Inner surfaces 48 of carriers 46 are configured to support a plurality of terminal contacts 44 crimped to ends of the electrical conductors 34 in spaced, electrically isolated side-by-side relation. According to the illustrated construction, terminal contacts 44 are arranged on carriers 46 in a pattern corresponding to the pattern of conductive contact pads 42 on sensing element 40. Thus, terminal contacts 44 are in substantially aligned contact with contact pads 42 with lateral separation between the terminal contacts maintained by spacing slots formed in surface 48 of carriers 46.

As shown, the terminal contacts 44 are elongated metal strips with curved ends and a protruding tang to releasably secure the terminal contacts to the inner surface 48 of carriers 46. The terminal contacts include a generally wave-like shape along their length characterized by alternating elevated and depressed zones. Such a wave-like surface provides multiple contact areas for contacting interface with conductive contact pads 42. The wave-like surface character also causes terminal contacts 44 to have a generally spring-like property to promote and maintain electrical contact with contact pads 42.

In the exemplary construction illustrated in FIG. 1, carriers 46 are substantially open across inner surface 48 facing the inner surface 48 of the other carrier. Terminal contacts 44 on each carrier 46 are supported in facing relation to terminal contacts 44 on the other carrier 46 to cooperatively define a female receptacle to receive the distal end 23 of sensing element 40 in sandwiched relation. Terminal contacts 44 are substantially aligned with contact pads 42 as seen in FIG. 2. Thus, terminal contacts 44 are held in contacting relation with contact pads 42 between the distal end 23 of sensing element 40 and inner surfaces 48 of the overlying carrier 46. Maintaining this connection permits transmission of electrical signals between contact pads 42 and terminal contacts 44 connected to conductors 34.

A discontinuous rectangular metallic retaining band 52 is disposed surrounding carriers 46. As will be explained, band 52 aids in assembly, and is involved in the loading of the carriers 46 toward the contact pads 42.

As best seen through reference to FIGS. 2 and 3, band 52 has a generally rectangular configuration with planar top and bottom wall 51, which is seen in the drawings. One side wall 43 extends between walls 51 and includes a pair of oppositely directed slots. These slots impart a degree of flexibility to permit deflection, and movement of walls 51 toward their associated carriers 46. The other sidewall is discontinuous and is defined by side wall segments 45. These segments assist in retention of the retaining band 52 in position about carriers 46.

Top and bottom walls 51 each overlie an outer planar surface 47 of one of the carriers 46. The spacing between planar walls 51 is such that the carriers 46 are sufficiently spaced apart to receive the distal end of sensing element 40 with contact pads 42 in aligned contact with terminal contacts 44. The slotted and segmented side wall (53 and 45) are sufficiently resilient to permit movement of walls 51 toward the back surfaces 47 of carrier 46.

To avoid disruption in signal transmission, it is desirable to maintain secure electrical contact between contact pads 42 and terminal contacts 44. Toward that end, a biasing bracket 50 shown in detail in FIGS. 2-4 surrounds carriers 46 with the distal end of sensing element 40 containing contact pads 42 sandwiched between the facing inner surfaces 48. Bracket 50 provides a continuous biasing force pressing carriers 46 toward the planar surfaces of sensing element 40.

In accordance with the instant disclosure, biasing bracket 50 provides a continuous biasing force pressing carriers 46 toward one another, thereby maintaining a secure electrical connection. As best seen through reference to FIGS. 2 and 3, the biasing bracket 50 is in the form of a two-piece unit incorporating a first bracket element 54 and a second bracket element 56. In the illustrated construction, first bracket element 54 and second bracket element 56 are substantially identical in construction having a substantially "U" shaped structure including a base wall 60, a first side wall 62 projecting from base wall 60 and a second side wall 64 disposed in substantially opposing relation to first side wall 62. First side wall 62 includes a window 66 defining a through opening with a locking edge 67. Second side wall 64 includes a latching flap 68 deformed outwardly relative to the plane of second side wall 64 such that a free distal edge 70 of latching flap 68 is disposed outboard from the plane of second side wall 64.

As seen through reference to FIGS. 3 and 4, first bracket element 54 and second bracket element 56 are connected with the side walls 62 and 64 of one bracket element 54 or 56 extending toward the other bracket element with first side wall 62 of each bracket element disposed to the outside of the second side wall 64 of the opposing bracket element. Upon assembly, free distal edges 70 of each latching flap 68 project outwardly through complementary windows 66 of the opposing bracket element. The engagement of distal edges 70 of latching flaps 68 with locking edges 67 in windows 66 connects the bracket elements to form a connected unit. In the assembled condition, biasing bracket 50 provides a containment volume adapted to substantially surround and hold carriers 46 with contact terminals 44 in electrical contact with contact pads 42.

Of course, the locked engagement of bracket elements may also be achieved, or augmented, by other techniques such as by welding the bracket elements together or by other physical attachment.

In the illustrated construction utilizing a pair of interlocking bracket elements, a stable connection between first bracket element 54 and second bracket element 56 in surrounding relation to carrier 46 is maintained by holding biasing bracket 50 in a state of tension such that first bracket element 54 and second bracket element 56 are urged continuously away from one another. According to the illustrated construction, such a tensioning relation is maintained by spring structures 80 defined at base wall 60 of bracket elements 54 and 56.

Spring structure 80 includes an arrangement of biasing elements or leaf springs 82 integral with base wall 60 of each bracket element and deformed inwardly in the same direction as side walls 62 and 64 from the plane of base wall 60 toward the interior containment portion of the bracket 50. In such a construction, biasing elements 82 are compressed in a zone between base wall 60 and band 52 when elements 54 and 56 of biasing bracket 50 is assembled around carriers 46. This compression causes first bracket element 54 and second bracket element 56 to be urged away from one another. First bracket element 54 and second bracket element 56 are thus held in locking relation relative to one another with the free distal edge 70 of latching flap 68 of one bracket element engaged against locking edge 67 of the associated window 66 of the other bracket element.

Deformation of the leaf springs 83 toward the plane of base walls 60 cause compressive forces to be imparted by spring structures 80 to urge carriers 46 toward the distal end 23 of sensing element 40. These forces are distributed along outer planar surfaces 47 of carriers 46 by the planar top and bottom walls 51 of band 52.

Bracket elements 54 and 56 are illustrated as identical components. Such configuration lends itself to manufacture of the brackets as metal stampings. It is also contemplated, however, that the bracket elements could be made as telescoping, with the side walls 62 and 64 of one bracket element arranged to be received between the side walls 62 and 64 of the other bracket element. Also, in such a construction, one of the bracket elements could include windows 66 and the other could include latching flaps 68.

As shown, the spring structures 80 utilize a pair of opposing biasing elements 82 in the form of leaf springs projecting inwardly from base wall 60 of first bracket element 54 and second bracket element 56. However, it is likewise contemplated that any number of other constructions may also be utilized. By way of example only, and not limitation, the number and form of biasing elements may be readily adjusted as desired. Likewise, although the illustrated construction makes use of four biasing elements, a greater or lesser number may be utilized as desired. Accordingly, a simple construction may utilize a spring structure having one or more biasing elements disposed at only one bracket element. An alternative construction may utilize a single biasing element at each bracket element. Yet another alternative construction may utilize a pair of biasing elements at one bracket element and a single biasing element at the opposing bracket element.

Regardless of the number or form of the biasing elements, upon assembly of biasing bracket 50 around carriers 46, biasing elements 82 provide a compressive reaction force upon planar top and bottom walls 51 of band 52 that operates against carriers 46. That is, as biasing elements 82 are deformed outwardly toward alignment with base wall 60, those biasing elements develop a restoring force which is applied to carriers 46 through band 52. This compressive force urges carriers 46 and the supported terminal contacts 44 toward aligned contact pads 42 disposed at distal end 23 of sensing element 40. Electrical contact is thereby maintained The resilient nature of biasing elements 82, ensures that this contacting relation is maintained even in adverse operating environments.

An exemplary process for assembly of a multi-lead electrical connection within sensor 10 may be understood through reference to FIGS. 1-4. It is contemplated that in assembly of the sensor assembly 10 the sensing element 40 is secured within the housing 20 with the distal end 23 with contact pads 42 extending toward conductor exit end 21. The conductors 34 comprise a bundle of insulated wires having a terminal plug (not shown) attached at one end. The other ends of each of conductors 34 is attached to a terminal contact 44 by a crimp connection. The assembly process contemplates placing the terminal contacts 44 in electrical conductive contact with contact pads 42.

The terminal contacts 44 are secured to the inner surfaces 48 of carrier 48 with the curved ends and protruding tangs releasably attached to the carrier 46 to hold each of the terminal contacts 44 within the spaced slots to ensure physical separation.

With carriers positioned with the terminal contacts 44 in facing relation, retaining band 52 is placed around the carriers. It is contemplated that the carriers 46 are temporarily held in spaced relation by a removable and disposable plastic plug 90 shown in FIG. 5 which is a pre-assembly component. Plug 90 may be made of metal or plastic or any suitable material. The separation of carriers 46 by plug 90 would be somewhat less than the thickness of the distal end 23 of the sensing element 40 carrying contact pads 42. Plug 90 may include overturned portions which temporarily attach the plug to carriers 46 prior to its removal for insertion of sensing element 40. The plug 90 is removed before insertion of the sensing element 40 between the carriers 46.

Retaining band 52 is positioned about the assemblage of carriers 46 held in spaced facing relation by removable pre-assembly plug 90. Each of planar top and bottom walls 51 overlie one of the outer planar surfaces 47 of one of the carriers 46. The slotted side wall 53 is of a length that a slight compressive load is imparted to the outer planar surface 47 of carriers 46 to urge them against the removable plastic plug 90.

Biasing bracket elements 54 and 56 are then positioned overlying the retaining band 52. The elements 54 and 56 are urged toward each other to engage the latching flap 68 of each bracket element with the window 66 of the other bracket element. The length of side walls 62 and 64 of the bracket elements 54 and 56 and the location of the free distal edge 70 and locking edge 67 of the latching flaps 68 and windows 66 determine the deflection of the biasing elements 82 of spring structures 80 relative to base walls 60. Such deflection, in turn, determines the magnitude of the biasing force imparted to the carrier 42 through planar top and bottom walls 51 of retaining band 52. With the thickness of the removable plug 90 somewhat less than the thickness of the end of sensing element 40, the force retaining plug is readily overcome to remove the plug during the assembly step of placing the terminal contacts 44 in electrically conductive contact with contact pads 42.

To accomplish completion of the conductive path from the sensing screen or surface 41 of the sensing element 40 to the electrical conductors 34, the plug 90 is removed, and the distal end 23 of the sensing element 40 with contact pads 42, is inserted between carriers 46. The terminal contacts 44 are disposed in electrically conductive contact with the contact pads 42.

The thickness of the sensing element 40 determines the deflection of the biasing elements 82 or leaf springs. Consequently this deflection establishes the compressive load or force imparted through planar top and bottom walls 51 of retaining band 52 urging the carriers 46 toward the captured distal end 23 of the sensing element 40. This loading imparts the requisite force to maintain the integrity of the electrically conductive connection between the terminal contact 44 and contact pads 42.

In the exemplary assembly process, two carriers 46 are arranged such that open faces of the carriers project toward each other. Each of the carriers 46 supports a plurality of terminal contacts 44. Distal end of sensing element 40 including the pattern of contact pads 42 is placed in sandwiched relation between carriers 46 such that terminal contacts 44 are disposed in contact with contact pads 42. Rectangular band 52 is thereafter placed in banding relation around carriers 46, thus holding sensor element 40 in sandwiched relation between carriers 46. With carriers 46 held in banded relation around sensor element 40, elements of biasing biasing bracket 50 may be assembled around carriers 46 and band 52. Elements of biasing bracket 50 may be lockingly engaged or otherwise physically joined to maintain an assembled condition. In the assembled condition, biasing elements 82 projecting inwardly from biasing bracket 50 are deformed toward base walls 60 and retained in compression between carriers 46 and biasing bracket 50. The biasing elements 82 provide a biasing compressing force to carriers 46 through walls 51. This compressing force urges carriers 46 continuously inwardly toward sensing element 40 to maintain electrically conductive contact between terminal contacts 44 and contact pads 42.

INDUSTRIAL APPLICABILITY

Sensor assemblies consistent with the present disclosure may be particularly well adapted for use in environments subject to vibration or other applied forces and/or to sensor assemblies intended to undergo future refurbishment.

In practice, a sensor assembly consistent with this disclosure may be utilized in environments such as engine exhaust monitoring, industrial equipment, transportation vehicles and the like where substantial durability and resistance to vibration is required. In such environments of use, the biasing containment bracket continuously urges the terminal contacts toward the conductive pads. The positional orientation and conductive contact is thus maintained in spite of vibration forces. Following a useful lifespan, the biasing containment bracket may be disassembled or cut away to permit refurbishment or replacement of the sensing element, terminal contacts, electrical conductors or other components.

It will be appreciated that the foregoing description provides examples of the disclosed system and technique. However, it is contemplated that other implementations of the disclosure may differ in detail from the foregoing examples. All references to examples herein are intended to reference the particular example being discussed at that point and are not intended to imply any limitation as to the scope of the disclosure or claims more generally. All language of distinction and disparagement with respect to certain features is intended to indicate a lack of preference for those features, but not to exclude such from the scope of the claims entirely unless otherwise indicated.

Accordingly, this disclosure contemplates the inclusion of all modifications and equivalents of the subject matter recited in the appended claims as permitted by applicable law. Moreover, any combination of the above-described elements in all possible variations thereof is contemplated unless otherwise indicated herein or otherwise clearly contradicted by context.

I claim:

1. A connector for a sensor assembly comprising:
a sensing element having a non-conductive body including a plurality of spaced conductive contact pads arranged thereon;
a plurality of conductive terminal contacts, each one being in contact with one of said spaced contact pads;
at least one carrier supporting said terminal contacts in contacting relation to said contact pads;
a containment bracket surrounding said at least one carrier and said contact pads;
said bracket including at least one biasing element extending from said bracket toward said at least one carrier urging said at least one carrier toward said contact pads.

2. The connector for a sensor assembly as recited in claim 1, wherein two carriers support said terminal contacts in contacting relation with said contact pads.

3. The connector for a sensor assembly as recited in claim 2 wherein said bracket includes a pair of spaced base walls, each overlying one of said carriers, at least one biasing element extending from one base wall toward one of said carriers and at least one biasing element extending from the other base wall toward the other of said carriers.

4. The connector for a sensor assembly as recited in claim 3 further including a retaining band including a top wall interposed between one of said carriers and one of said at least one biasing elements and a bottom wall interposed between another of said at least one biasing elements and the other of said carriers.

5. The connector for a sensor assembly as recited in claim 4 wherein said sensing element, said carriers, and said top and bottom walls of said band are substantially planar and said band includes slotted side walls.

6. The connector for a sensor assembly as recited in claim 4, wherein each of said base walls include at least one leaf spring deformed from the plane of said base wall toward an associated carrier.

7. The connector for a sensor assembly as recited in claim 6 wherein each said base wall includes a pair of leaf springs deformed from the plane of said base wall toward an associated carrier.

8. The connector for a sensor assembly as recited in claim 4, wherein said bracket includes a pair of relatively connected, separable bracket elements.

9. The connector for a sensor assembly as recited in claim 8, wherein said bracket elements each include a pair of side walls projecting away from one of said base walls, one of said side walls having an outwardly projecting latching flap defining a free distal edge, the other of said side walls having a window opening including a locking edge in retaining contact with said free distal edge of said other bracket element.

10. The connector for a sensor assembly as recited in claim 8 further including a retaining band including a top wall interposed between one of said carriers and one of said at least one biasing element and a bottom wall interposed between another of said at least one biasing element and the other of said carriers.

11. The connector for a sensor assembly as recited in claim 10, wherein said sensing element, said carriers and said top and bottom walls of said band are substantially planar and wherein said retaining band includes slotted side walls.

12. A sensor assembly comprising:
a sensor housing;
a connector within said housing comprising:
a sensing element having a non-conductive body including a plurality of spaced conductive contact pads arranged thereon;
a plurality of conductive terminal contacts, each one being in contact with one of said spaced contact pads;
at least one carrier supporting said terminal contacts in contacting relation to said contact pads;
a containment bracket surrounding said at least one carrier and said contact pads;
said bracket including at least one biasing element extending from said bracket toward said at least one carrier urging said at least one carrier toward said contact pads.

13. A sensor assembly as recited in claim 12 wherein two carriers support said terminal contacts in contacting relation to said contact pads, and wherein said bracket includes a pair of spaced base walls, each overlying one of said carriers, at least one biasing element extending from one base wall toward one of said carriers and at least one biasing element extending from the other base wall toward the other of said carriers.

14. A sensor assembly as recited in claim 13 further including a retaining band including a top wall interposed between one of said carriers and one of said at least one biasing elements and a bottom wall interposed between another of said at least one biasing elements and the other of said carriers, and wherein said sensing element, said carriers, and said top and bottom walls of said band are substantially planar and said band includes slotted side walls.

15. A sensor assembly as recited in claim 13, wherein each of said base walls includes at least one leaf spring deformed from the plane of said base wall toward an associated carrier.

16. A sensor assembly as recited in claim 13 wherein said bracket includes a pair of relatively connected, separable elements, and wherein said bracket elements each include a pair of side walls projecting away from one of said base walls, one of said side walls having an outwardly projecting latching flap defining a free distal edge, the other of said side walls having a window opening including a locking edge in retaining contact with said free distal edge of said other of said bracket element.

17. A method of assembly for a sensor assembly having a connector for a sensor assembly, the steps comprising
providing a sensing element having a non-conductive body including a plurality of spaced conductive contact pads arranged thereon;
providing a plurality of conductive terminal contacts, for contact with one of said spaced contact pads;
providing at least one carrier for supporting said terminal contacts in contacting relation to said contact pads;
providing a containment bracket for surrounding said at least one carrier and said contact pads;
said bracket including at least one biasing element extending from said bracket and toward said at least one carrier for urging said at least one carrier toward said contact pads;
attaching said terminal contacts to said at least one carrier;
positioning said at least one carrier with said terminal contacts in contact with said plurality of spaced contact pads;
surrounding said spaced contact pads and said at least one carrier with said containment bracket; and
causing said at least one biasing element to urge said at least one carrier toward said spaced contact pads of said sensing element.

18. A method of assembly for a sensor assembly as recited in claim 17, further including applying a band in surrounding relation to said spaced contact pads and said at least one carrier between said at least one biasing element and said at least one carrier.

19. A method of assembly for a sensor assembly as recited in claim 18 wherein said connector includes two carriers supporting said terminal contacts and bracket includes a pair of separable bracket elements, each said bracket element including a base wall including at least one leaf spring deformed from the plane of said base wall, the steps further comprising connecting said separable bracket elements in surrounding relation to said band, and compressing said at least one leaf spring of each said bracket element against said band.

20. A method of assembly for a sensor assembly as recited in claim 19 wherein said separable bracket elements each include a pair of side walls projecting away from said base wall, one of said side walls having an outwardly projecting latching flap defining a free distal edge, the other of said side walls having a window opening including a locking edge, the steps further comprising connecting said separable bracket elements together with said free distal edge of said projecting latching flaps in contact with said locking edge of said windows in said side wall of the other bracket element.

* * * * *